United States Patent [19]

Moriconi

[11] 4,417,460

[45] Nov. 29, 1983

[54] HYPODERMIC SYRINGE DESTRUCTION DEVICE

[76] Inventor: Dario J. Moriconi, 6616 La Miroda Dr., Apt. #1, Jacksonville, Fla. 32117

[21] Appl. No.: 241,561

[22] Filed: Mar. 9, 1981

[51] Int. Cl.³ .............................................. B21D 28/00
[52] U.S. Cl. ....................................... 72/325; 72/330; 83/167; 83/925 R; 30/124
[58] Field of Search ................................ 72/324–326, 72/330–332, 337, 338, 430; 30/124, 131, 134; 83/167, 925 R

[56] References Cited

U.S. PATENT DOCUMENTS

| | | | |
|---|---|---|---|
| 1,232,050 | 7/1917 | Kraemer | 72/430 |
| 1,887,732 | 11/1932 | Pagel et al. | 72/324 |
| 3,427,837 | 2/1969 | Faulconer | 72/430 |
| 3,469,750 | 9/1969 | Vanderbeck | 30/131 |
| 3,585,835 | 6/1971 | Clement | 72/330 |
| 3,785,233 | 1/1974 | Robinson | 83/167 |
| 4,255,996 | 3/1981 | Choksi et al. | 83/167 |
| 4,275,628 | 6/1981 | Greenhouse | 83/167 |

FOREIGN PATENT DOCUMENTS 2064915  6/1972  Fed. Rep. of Germany ........ 72/325

*Primary Examiner*—Daniel C. Crane
*Attorney, Agent, or Firm*—C. A. Phillips

[57] ABSTRACT

A hypodermic syringe destruction device wherein a cutting member and hammer member are positioned on a movable carrier within a housing. A fixed anvil is mounted within the housing, and an opening in the housing is arranged to permit the needle end of a hypodermic syringe to be inserted in an open region between the anvil and blade-hammer, with the movable carrier in a normal position. A solenoid is mechanically coupled to the carrier to move the blade through the syringe and hammer across the needle and anvil, whereby the needle region of the hypodermic syringe is separate from the syringe portion, and the needle is bent essentially 90°.

1 Claim, 3 Drawing Figures

HYPODERMIC SYRINGE DESTRUCTION DEVICE

TECHNICAL FIELD

This invention relates to devices for preventing the reusage of hypodermic syringes, and particularly to a device which severs the syringe and bends its needle.

BACKGROUND ART

As is known, hypodermic syringes are legitimately used on a very large scale in hospitals and doctors' offices by professional health care personnel. Remaining, however, is the illegal use of hypodermic syringes by persons administering to themselves or to others illicit drugs. Under these circumstances, it is, of course, important to limit access by those who would use hypodermic syringes illegally.

It is thus desirable that after a hypodermic syringe has been used by a health care personnel that it be destroyed. Destruction is equally important to prevent the spread of a contagious disease which might infect a hypodermic needle, and to prevent the residue of a dangerous medication on a hypodermic needle from being brought into harmful contact with someone who might later handle or use the syringe.

Accordingly, it is the present practice of hospitals and some doctors' offices to employ means to effect, at least to a degree, the destruction of hypodermic syringes. Perhaps the most common type used is a hand-operated device wherein the syringe is severed from the needle portion of the hypodermic syringe. A difficulty with this device is that it is hand-operated and requires quite a bit of hand pressure.

Another device for the destruction of hypodermic syringes grinds them, both plastic and metal. A difficulty with this type device is that it is noisy and it is not generally used on a hospital ward for this reason. This means that hypodermic needles have to be gathered in a ward and taken to the device, which requires that there be additional handling of the syringes, which is not desirable.

DISCLOSURE OF THE INVENTION

In accordance with the present invention, a hypodermic syringe destruction device is constructed in which a combination blade and hammer is mounted on a movable frame within a housing. The needle end region of a hypodermic syringe is inserted into the housing through an opening, and then by means of a solenoid, the movable frame moves the blade and hammer across the hypodermic needle, severing it from the syringe portion and effecting a bending operation of the needle, the latter being effected by means of an anvil against which the needle is pressed by the hammer.

DETAILED DESCRIPTION OF THE DRAWINGS

Figure 1:
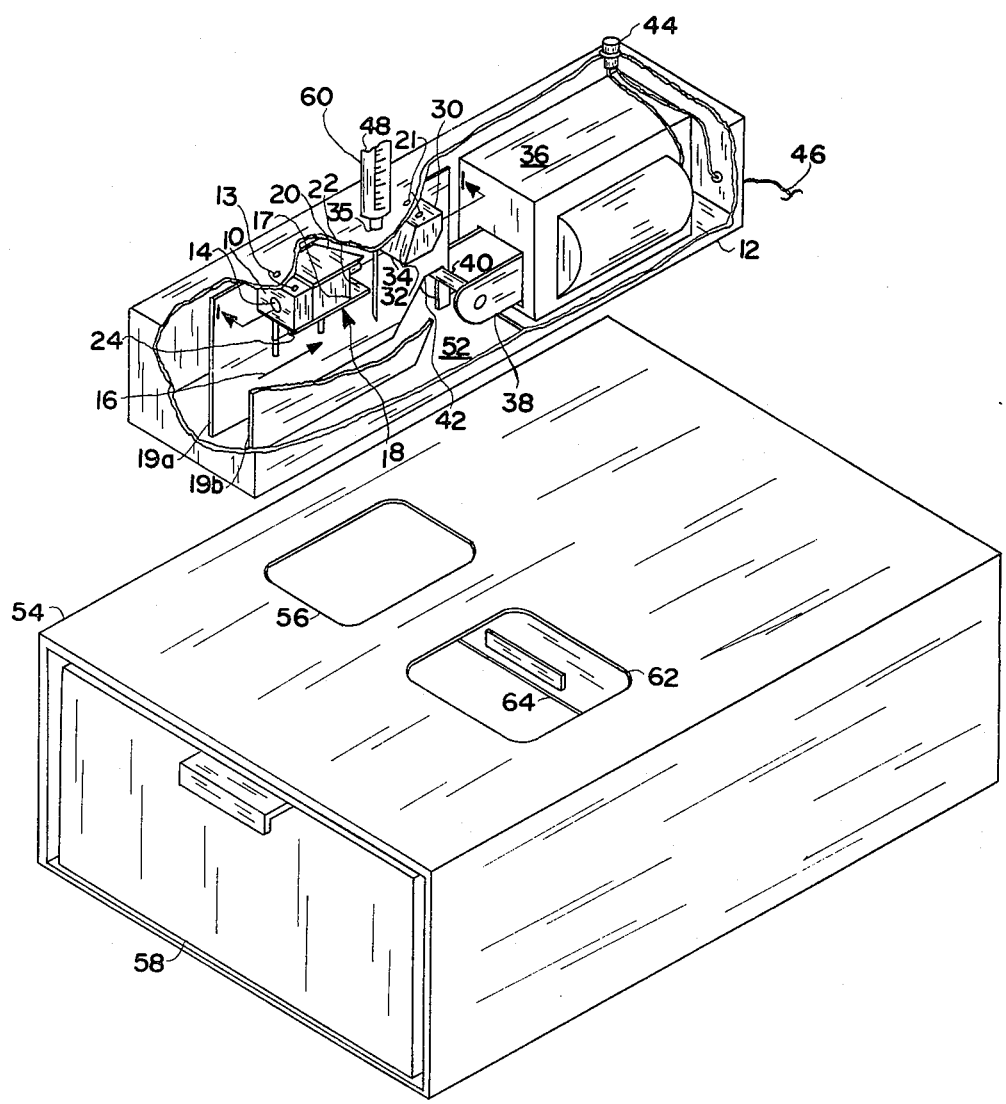
FIG. 1 is an exploded pictorial view of an embodiment of the invention.

Referring to the drawings, fixed guide 10 is attached to housing 12 by rivets 13, and guide 10 contains a cylindrical guide member 14 which extends through opening 15 of block 17, which in turn supports plates 19a and 19b of carrier 18. In this manner, directional movement of carrier 18 is effected in the direction of arrow 16. Carrier 18 supports (by means not shown) blade 20 and hammer 22. Normally, carrier 18 is biased to the left by spring 24 connected between arm 26 on fixed guide 10 and arm 28 on block 17.

Figure 2:
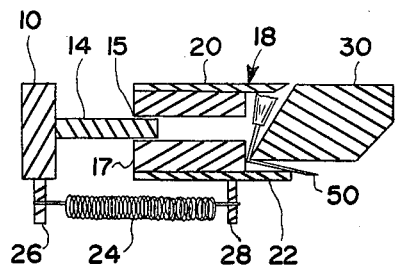
FIG. 2 is a sectional fragmentary view illustrating the operation of the device.

Anvil 30 is fixedly attached to housing 12 by rivets 21 and includes a downwardly tapered surface 32 and a laterally extending edge 34, the latter being perpendicular to the direction of arrow 16 and perpendicular to the axis of opening 35 of housing 12 through which a hypodermic syringe is inserted. Solenoid 36, fixedly attached to housing 12, includes a movable arm 38 with a pin 40 which engages slots 42 in plates 19a and 19b of carrier 18 to pull carrier 18 to the right upon solenoid 36 being energized. Solenoid 36 is then energized by button switch 44 connected in energizing power cord lead 46. In operation, hypodermic syringe 48 would be positioned through opening 35 in housing 12 as shown in FIG. 1. Then, button switch 44 would be operated, and this would cause carrier 18 to be moved to the right, causing blade 20 to sever syringe 48 and cause hammer 22 to move under the edge of anvil 30 in a spaced relationship thereto in order to bend needle 50 of the syringe in an essentially 90° bend, as shown in FIG. 2.

Upon being severed and after the release of button 44, enabling carrier 18 to be moved back to the left, needle 50 would then drop down through opening 52 in housing 12.

Housing 12 is mounted on a storage housing 54 (by means not shown). Opening 52 and opening 56 of storage housing 54 are aligned, and thus when severed, needle 50 would drop through opening 56 into disposable container 58. The severed upper portion 60 of syringe 48 would then be deposited by hand through an opening 62, and thus into disposable container 58. Opening 62 has a cover 64, which would normally be moved to the left to cover this opening.

Figure 3:
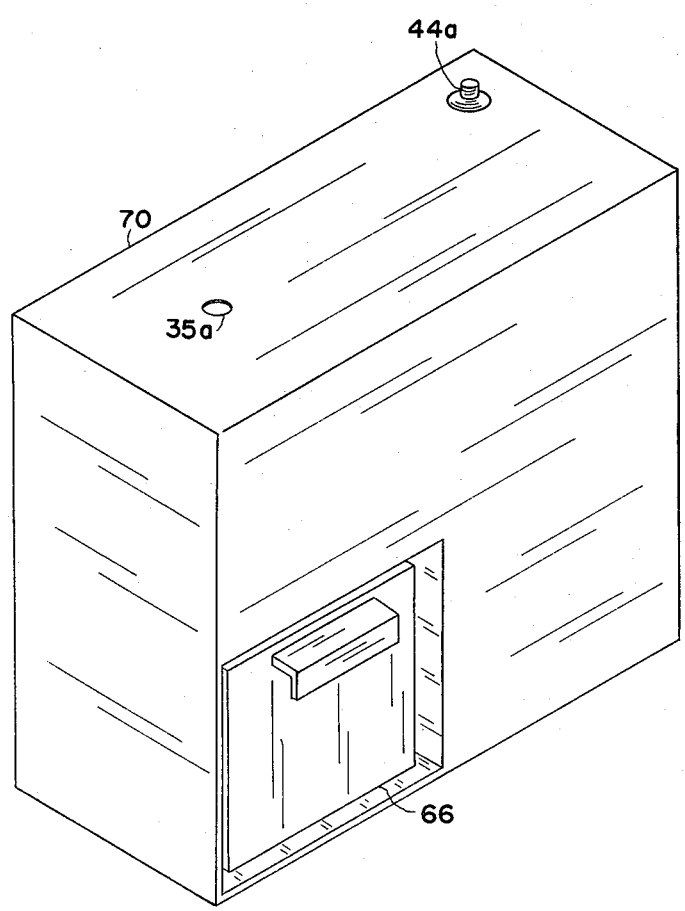
FIG. 3 is pictorial view of an alternate configuration of the housing of the device.

FIG. 3 illustrates a modification of the device as shown in FIG. 1 wherein housing 70 is smaller than housing 54, and wherein removable container 66 is likewise smaller. The use of this version of the device is the same as with the other version. Thus, with a hypodermic needle being placed into an opening 35a, and switch 44a operated, the destruction of a hypodermic needle as described above would be effected.

I claim:

1. A hypodermic syringe destruction device for severing a syringe portion and bending a needle of a hypodermic syringe comprising:

a housing having an upper side and an opening in said upper side through which the needle end region of a hypodermic syringe may be generally vertically inserted downward, said opening having an axis with the syringe being insertable through said opening parallel to said axis;

a movable support within said housing and immediately below said upper side and supported by said housing for linear movement generally horizonally and transverse to said axis of said opening;

a blade attached to said movable support and lying in a generally horizontal plane and having an oblique edge which passes across and just under said opening in said upper side of said housing;

a hammer supported on said movable support and spaced below said blade, said hammer and support being generally L-shaped in cross section with said support forming a generally vertical wall facing the axis of said opening and with said hammer comprising a lower, generally horizontal plate extending outward from said generally vertical wall;

an anvil having a horizontal upper surface fixedly attached to the inside of said housing on the opposite side of said opening from said movable support and having a sloping surface which generally faces the vertical axis of said opening but slopes downward toward said vertical axis and having a generally horizontal lower surface at an elevation just above the upper surface of said lower plate of said hammer with said horizontal lower surface being spaced from the upper surface of said lower plate sufficient to bend the syringe needle therebetween, said anvil being opposite said support such that said anvil horizontal upper surface is coplanar with said blade lying in a horizontal plane and said sloping surface exgtends in a continuous manner from said horizontal upper surface to said horizontal lower surface;

operating means for selectively moving said movable support toward said anvil comprising a solenoid having a body region attached to said housing and a movable arm attached to said movable support, whereby, when a hypodermic syringe needle is inserted into said opening and said solenoid is operated, said L-shaped portion of said hammer bends the needle around said lower surface of said anvil, and a portion of the syringe holding said needle is supportable against the sloping surface of said anvil and is severed by said edge of said blade; and a container positioned to receive the severed needle end region of a hypodermic syringe.

* * * * *